United States Patent [19]
Walters

[11] Patent Number: 5,305,733
[45] Date of Patent: Apr. 26, 1994

[54] TRIGGER TO ACTIVATE SUPERCOOLED AQUEOUS SALT SOLUTION FOR USE IN A HEAT PACK

[75] Inventor: Dale E. Walters, St. Louis, Mo.

[73] Assignee: Omni Therm, Inc., St. Louis, Mo.

[21] Appl. No.: 40,475

[22] Filed: Mar. 31, 1993

[51] Int. Cl.⁵ ............................ A61F 7/00; A61F 7/08
[52] U.S. Cl. ................................ 126/263 R; 126/204
[58] Field of Search ............... 126/204, 263; 128/403; 62/4

[56] References Cited

U.S. PATENT DOCUMENTS

| | | | |
|---|---|---|---|
| 1,384,747 | 7/1921 | Eckelmann et al. | 126/263 |
| 1,433,010 | 10/1922 | Hogan . | |
| 1,915,523 | 6/1933 | Ferguson . | |
| 2,220,777 | 11/1940 | Othmer . | |
| 2,289,425 | 7/1942 | Hogan . | |
| 2,916,886 | 12/1959 | Robbins | 126/263 X |
| 3,093,308 | 6/1963 | Snelling . | |
| 4,077,390 | 3/1978 | Stanley et al. . | |
| 4,572,158 | 2/1986 | Fiedler . | |
| 4,604,987 | 8/1986 | Keltner | 126/204 |
| 4,688,572 | 8/1987 | Hubbard et al. | 126/204 |

*Primary Examiner*—Carl D. Price
*Attorney, Agent, or Firm*—Kalish & Gilster

[57] ABSTRACT

A trigger to initiate crystallization of a supercooled aqueous salt solution of a heat pack, thereby liberating heat. The trigger, when activated, pierces the container, allowing air to enter the pack and initiate crystallization of the solution. A seal over the trigger prevents the solution from leaking from the heat pack.

12 Claims, 3 Drawing Sheets

TRIGGER TO ACTIVATE SUPERCOOLED AQUEOUS SALT SOLUTION FOR USE IN A HEAT PACK

FIELD OF THE INVENTION

This invention relates to a trigger to activate a supercooled aqueous salt solution wherein the solution is encased in a flexible container to form a heat pack, and more particularly an arrangement in which the trigger is affixed to the exterior of the flexible container. Crystallization is initiated when the trigger is activated and pierces the container, exposing the solution to air, and heat is liberated.

BACKGROUND OF THE INVENTION

Heat packs utilizing supercooled aqueous salt solutions have been used for some time for the treatment of soreness of muscles of athletes and sportsman in localized areas. Heat packs are used also as infant heel warmers in medical facilities as an aid in drawing blood. From the simple hot water bottle we have progressed upward to the use of supercooled aqueous salt solutions wherein not only the temperatures can be controlled but so also the duration of the heat given off. Various solutions such as sodium acetate and calcium nitrate tetrahydrate are examples of such solutions.

Various techniques of initiating crystallization have been proposed, including inserting a crystal of material into the supercooled solution, and scraping some metal inside the container to introduce impurities into the supercooled solution. Examples of these techniques are disclosed in the following U.S. Pat. Nos. 1,433,010, 2,289,425, 2,220,777, 3,093,308, 4,077,390 and 4,572,158. U.S. Pat. No. 1,915,523 discloses the introduction of air into the solution by means of a valve. This complicated method involves the use of both hands to manipulate the valve.

The present invention provides a simple device that is easily manufactured and the trigger is easily activated. Of particular advantage is that the heat pack of the present invention can be initiated using one hand. Of further advantage is that a temperature indicator can be attached to the heat pack to indicate the appropriate temperature. A final advantage is that the heat pack can be secured to a body part, thereby simplifying its use.

SUMMARY OF THE INVENTION

Briefly, the present invention relates to a trigger to initiate crystallization of a supercooled aqueous salt solution encased in a flexible container, comprising a puncturing means and a sealing means, wherein the trigger is attached by a sealing means to the exterior of the flexible container, wherein the trigger, when activated, punctures the flexible container, and admits air thereby initiating crystallization, and wherein the sealing means prevents any leakage of the solution from the container. The flexible container, with the claimed trigger and the enclosed supercooled aqueous salt solution forms a heat pack.

BRIEF DESCRIPTION OF THE DRAWINGS

The above advantages may be more clearly understood from the following detailed description and by reference to the drawings.

DETAILED DESCRIPTION OF THE PREFERRED EMBODIMENT

Figure 1:
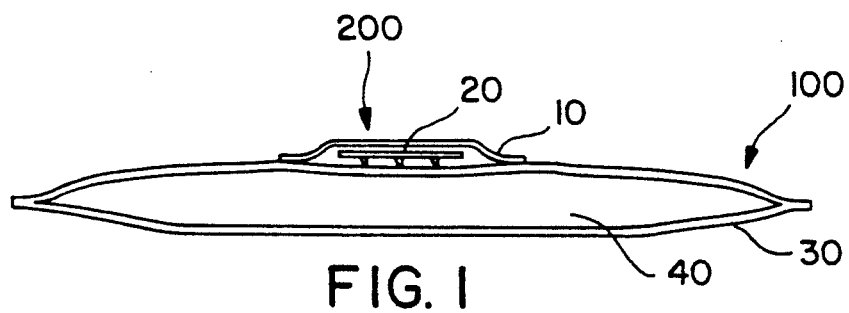
FIG. 1 is a side, sectional view of the heat pack, wherein the trigger is not activated.

Referring to FIG. 1, a heat pack 100 having a trigger 200 made of a puncturing means 20 secured to the exterior of a flexible container 30 by means of a seal 10, wherein the container holds a supercooled salt solution 40 which, when activated, releases heat. Suitable solutions include supercooled sodium acetate, lead acetate, calcium nitrate tetrahydrate, sodium pyrophosphate and sodium thiosulfate. The preferred solution is sodium acetate, which is generally harmless to humans.

The salt solution 40 is made by dissolving the salt in the desired amount of water. The amount of salt to be utilized should permit the salt solution to be supercooled to at least the ambient temperature at which the heat pack is intended to be utilized. Additionally, the amount of salt should not be so great that the resulting solution is activated unintentionally by shaking, etc., when at ambient or use temperature. For example, if the heat pack is to be utilized at 0° C., then the amount of salt used should permit supercooling of the salt solution down to at least that temperature and the solution should be relatively stable at that temperature. However, sufficient salt should be used to enable the supercooled solution to be readily crystallized when the trigger 20 is activated.

The amount of water present in the salt solution will vary depending upon the heat pack temperature desired. As the amount of water increases relative to the amount of salt, the temperature to which the container contents are raised when the salt crystallizes decreases. This means that the maximum temperature of a heat pack 100 embodying the invention can be controlled by appropriate adjustment of the water/salt ratio.

Flexible container 30 (FIG. 1) of heat pack 100 can be made from any flexible material not affected by the supercooled solution, and impermeable to it. Additionally, the container material must be able to withstand the temperatures (generally on the order of about 60° to 65° C.) to which the heat pack 100 is heated to redissolve the precipitated salt. Suitable materials include plastic materials such as rubber, vinyl, vinyl-coated fabric, nylon polylaminate and polyethylene. Preferably the flexible container is made from nylon polylaminate of a thickness in the range of about 1 mil (0.026 mm) to 10 mils (0.26 mm).

Figure 4:
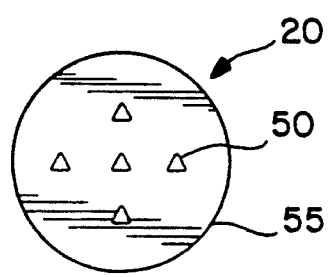
FIG. 4 is a bottom plan view of the trigger.

A trigger 200 is made of a puncturing means 20 is secured to the exterior of flexible container 30 by means of a seal 10. The puncturing means is any means suitable for manipulation against the flexible container for puncturing the container in response to such manipulation and thereby initiating crystallization of the solution. As shown in FIG. 4, examples of suitable puncturing means includes a base plate 55 with a plurality of piercing members 50 upstanding, i.e., protruding from the plate 55 and thus extending outwardly from the plane or body proper of plate 55 toward and contacting container wall 35. Preferably, the puncturing means constitutes a metal base plate having a plurality of piercing members being constituted by triangular or other pointed upset portions of the metal base plate. The preferred number of piercing members is in the range of about 3 to 10. The height of the piercing members is preferably in the range of about 10 mil (0.26 mm) to 150 mil (3.9 mm).

As shown in FIG. 4, plate 55 can be made of such solid materials as hard plastics and metals. Preferably, plate 55 is made of a ferrous material, such as stainless steel. More preferably, plate 55 may be formed of plated steel (e.g., by zinc or nickel galvanizing), and of circular shape. The preferred diameter of such plate is in the range of 0.25 inch (0.635 cm) to 1.5 inch (3.8 cm) and of sufficient thickness, preferably 0.008 in. (72 gauge) that the piercing members will not deform substantially upon the application of piercing pressure by such manipulation.

Sealing means 10 is any means suitable for adhering the puncturing means to flexible container 30 and preventing the leaking of the solution, or ensuring against such leakage, from the container, even though for reasons pointed out later the solution is not prone to leak through a puncture point. Such means includes a contact adhesive strip that covers the puncturing means, securing it against the container, a band encircling the container, or adhesive means applied between the puncturing means and the flexible container. The preferred means is an contact adhesive seal having a diameter greater than that of the trigger plate 55. The diameter of the seal is preferably in the range of 0.75 inches (1.80 cm) to about 2.0 inches (5.08 cm).

Figure 2:
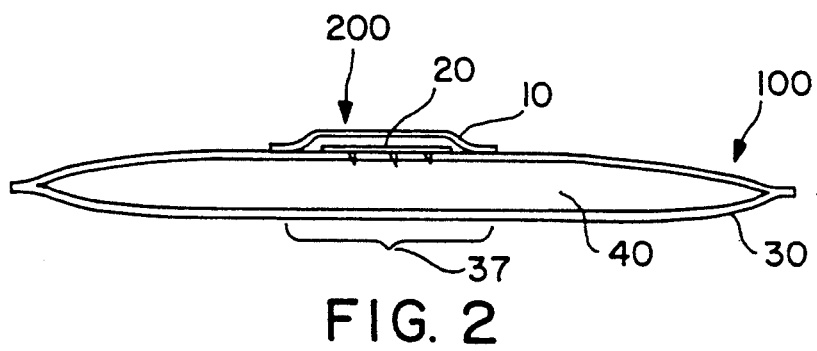
FIG. 2 is a side, sectional view of the heat pack, wherein the trigger is activated, i.e., the trigger has punctured the flexible container.

FIG. 2 shows a side sectional view of heat pack 100 wherein the trigger has been activated. Trigger 200 is activated by applying pressure to the puncturing means sufficient to puncture the flexible container. Such pressure can be accomplished by compressing the trigger between the thumb and index finger by placing the thumb under the container and the index finger over the trigger. The trigger can also be activated by pressing against the puncturing means while the heat pack is resting on a solid surface. A particular advantage of the present invention is that the heat pack is easily activated with one hand. The piercing members 55 are shown in FIG. 2 as piercing the flexible container 30, thereby allowing air to come in contact with the supercooled salt solution, precipitating the salt and initiating heating.

An insignificantly small amount, or no amount, of the supercooled salt solution may leak (if at all) from a puncture point. As exposure to oxygen molecules of even the small surface area of the solution represented by the puncture area of a single puncture element 50 may be sufficient to trigger precipitation. So also, exposure to oxygen changes the state of the solution at the puncture point so effectively and in such short time as to effectively provide self-sealing of the puncture point.

Figure 3:
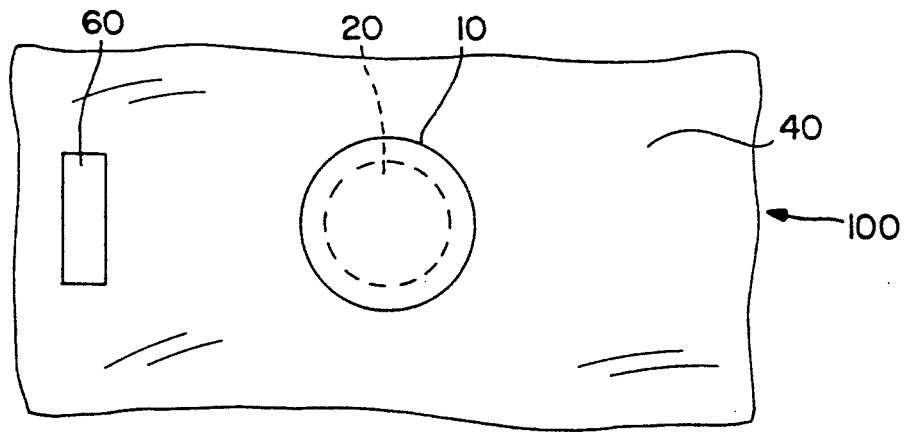
FIG. 3 is a top plan view of the heat pack.

FIG. 3 shows a top view of the heat pack 100 having a temperature indicator 60 affixed to exterior of the flexible container. The temperature indicator can be any indicator known in the art, preferably a liquid crystal indicator.

Figure 5:
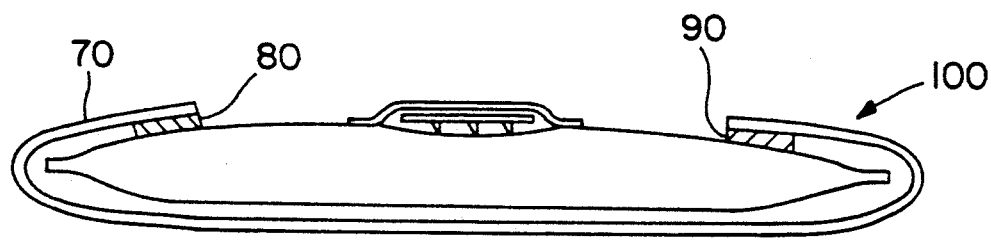
FIG. 5 is a side sectional view of the heat pack with a fastening means.

The heat pack of the present invention can be used to heat body parts, such as wrists, ankles and arms, or infant heel. In a preferred embodiment, the heat pack has a fastening means for securing the heat pack to a body part. The fastening means can be an elastic band, a contact adhesive applied to the bottom surface of the flexible container, or a strip which encircles the body part. The preferred fastening means is a strip which encircles the body part. As shown in FIG. 5, the strip can be adhesively attached to the heat pack 100 by an adhesive means 80. A flexible strap 70 is sufficiently long to encircle a body part, in the range of 2 inches (5.08 cm) to 6 inches (15.24 cm). The strap can be made of plastic or fabric, such as cotton cloth. Preferably, the strap is hypoallergenic, so as to not irritate the skin. At the opposite end of the strap is a contact adhesive or pressure sensitive adhesive 90 which is peeled from the flexible container and reapplied to the heat pack when the body part is encircled.

Figure 6:
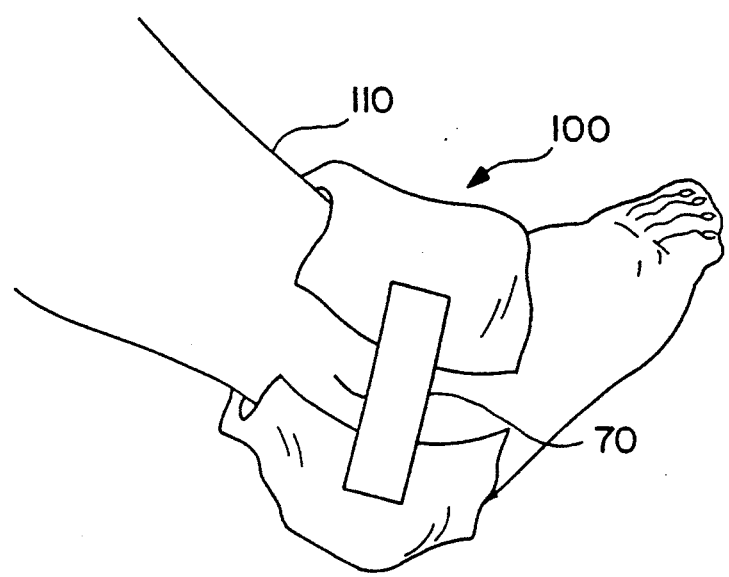
FIG. 6 is a side view of the heat pack fastened to an ankle.

In FIG. 6 an ankle 110 is encircled by the heat pack 100, which is fastened by flexible strap 70. The heat pack is held securely against the ankle by the strap, being thus unusually advantageous for use of the heat pack as an infant heel warmer.

Figure 8:
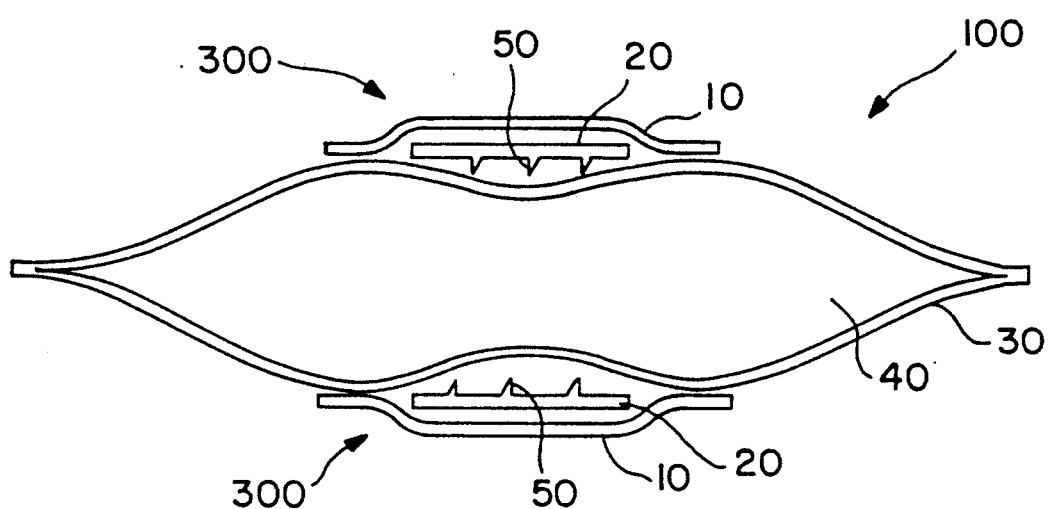
FIG. 8 is a side, sectional view of the heat pack, wherein the trigger is two puncturing means on opposite sides of the flexible container.

FIG. 8 discloses a heat pack 100 having a trigger 300 made of two puncturing means 20 on opposite sides of the flexible container 30, wherein the trigger is activated by applying pressure, causing the piercing members 50 to work against each other and puncture the container, thereby triggering precipitation of the salt.

Figure 7:
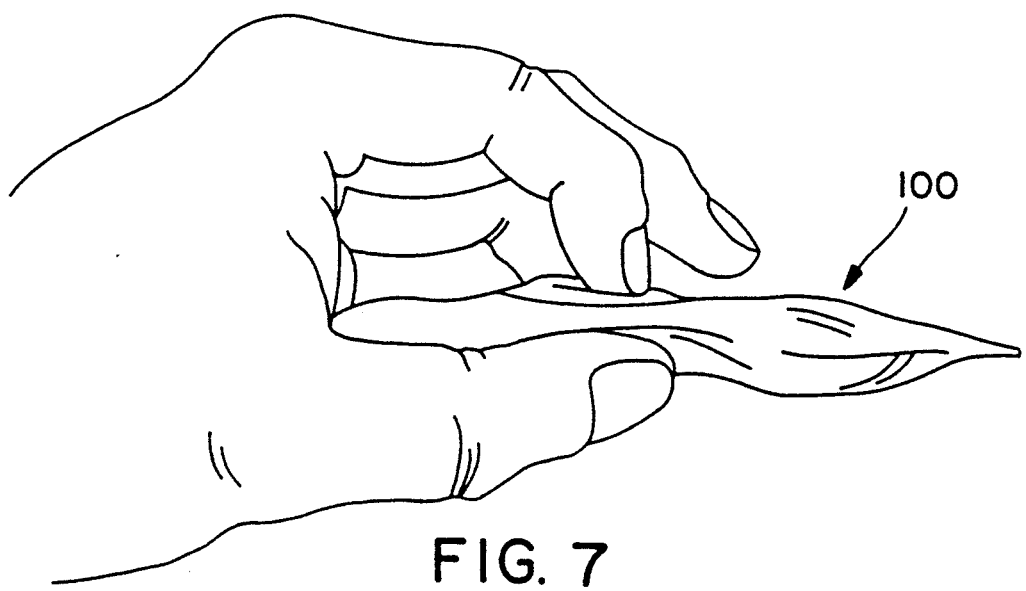
FIG. 7 illustrates manipulation of the heat pack for triggering its operation.

Typical operation is shown in FIG. 7. The user places pouch 30 between the thumb and index finger. Squeezing pressure against the opposite walls causes piercing and resultant activation by triggering of precipitation. One may alternatively rub the thumb nail over the adjacent surface to bring the opposite bag wall in contact with the piercing members.

The invention and its attendant advantages are understood from the foregoing description and it is apparent that various changes may be made in the form, construction and arrangement of the parts without departing from the spirit and scope thereof or sacrificing its material advantages, the arrangements described being merely by way of example. The claims of the invention are not restricted to the specific forms shown.

I claim:

1. A trigger to initiate crystallization of a supercooled aqueous salt solution encased in a flexible container, comprising a puncturing means and an adhesive sealing means, wherein the puncturing means is attached by a sealing means to the exterior of the flexible container, wherein the trigger, when activated, punctures the flexible container, and admits air thereby initiating crystallization, and wherein the sealing means prevents any leakage of the solution from the container.

2. The trigger of claim 1, wherein the salt of the supercooled aqueous salt solution is selected from the group consisting of sodium acetate, lead acetate, calcium nitrate tetrahydrate, sodium pyrophosphate and sodium thiosulfate.

3. The trigger of claim 1, wherein the flexible container is composed of materials selected from the group consisting of rubber, vinyl, vinylcoated fabric, nylon polylaminate and polyethylene.

4. The trigger of claim 1, wherein the puncturing means comprises a base plate carrying a plurality of piercing members.

5. The heat pack of claim 1, wherein attached to the exterior of the flexible container is a fastening means to secure the heat pack to a body part.

6. The heat pack of claim 5, wherein the fastening means is a strap which is attached using a contact adhesive or pressure sensitive adhesive.

7. The heat pack of claim 6, wherein affixed to the exterior of the heat pack is a liquid crystal temperature indicator.

8. The heat pack of claim 6, wherein the salt of the supercooled aqueous salt solution is selected from the group consisting of sodium acetate, lead acetate, calcium nitrate tetrahydrate, sodium pyrophosphate and sodium thiosulfate,
    wherein the flexible container is composed of materials selected from the group consisting of rubber, vinyl, vinylcoated fabric, nylon polylaminate and polyethylene,
    wherein the puncturing means comprises a base plate carrying a plurality of piercing members in upstanding relationship and extending toward and in contact with a wall surface of the flexible container for puncturing of the contacted wall surface upon manipulation of the flexible container, and
    wherein the sealing means is a contact adhesive seal having a diameter greater than that of the base plate.

9. The trigger of claim 1, wherein the trigger comprises two puncturing means on opposite sides of the flexible container, so that, when the puncturing means are manipulated, the piercing members work against each other to pierce the flexible container.

10. The trigger of claim 9, wherein a liquid crystal temperature indicator is attached to the flexible container.

11. A trigger to initiate crystallization of a supercooled aqueous salt solution encased in a flexible container, comprising a puncturing means and a sealing means,
    wherein the puncturing means is attached by a sealing means to the exterior of the flexible container,
    wherein the trigger, when activated, puncture the flexible container, and admits air thereby initiating crystallization,
    wherein the sealing means prevents nay leakage of the solution from the container,
    wherein the salt of the supercooled aqueous salt solution is selected from the group consisting of sodium acetate, lead acetate, calcium nitrate tetrahydrate, sodium pyrophosphate and sodium thiosulfate,
    wherein the flexible container is composed of materials selected from the group consisting of rubber, vinyl, vinylcoated fabric, nylon polylaminate and polyethylene,
    wherein the puncturing means comprises a base plate with a plurality of piercing members, and
    wherein the sealing means is a contact adhesive seal having a diameter greater than that of the base plate.

12. A trigger to initiate crystallization of a supercooled aqueous salt solution encased in a flexible container, comprising a puncturing means and an adhesive sealing means,
    wherein the puncturing means is attached by a sealing means to the exterior of the flexible container,
    wherein the puncturing means comprises a base plate carrying a plurality of piercing means,
    wherein the trigger, when activated, punctures the flexible container, and admits air thereby initiating crystallization, and
    wherein the sealing means prevents any leakage of the solution from the container.

* * * * *

UNITED STATES PATENT AND TRADEMARK OFFICE
CERTIFICATE OF CORRECTION

PATENT NO. : 5,305,733

DATED : Apr. 26, 1994

INVENTOR(S) : Dale E. Walters

It is certified that error appears in the above-identified patent and that said Letters Patent is hereby corrected as shown below:

Column 6, line 8, replace the word "nay" with the word --any--.

Signed and Sealed this

Sixteenth Day of August, 1994

Attest:

BRUCE LEHMAN

Attesting Officer     Commissioner of Patents and Trademarks